(12) United States Patent
Angotzi et al.

(10) Patent No.: US 9,848,792 B2
(45) Date of Patent: Dec. 26, 2017

(54) INTRACORTICAL-DETECTION DEVICE AND CORRESPONDING CONTROL METHOD

(75) Inventors: Gian Nicola Angotzi, Genoa (IT); Luciano Fadiga, Ferrara (IT); Giulio Sandini, Genoa (IT)

(73) Assignee: FONDAZIONE INSTITUTO ITALIANO DI TECHNOLOGIA (IT)

( * ) Notice: Subject to any disclaimer, the term of this patent is extended or adjusted under 35 U.S.C. 154(b) by 1051 days.

(21) Appl. No.: 14/125,058

(22) PCT Filed: Jun. 11, 2012

(86) PCT No.: PCT/IB2012/052948
§ 371 (c)(1),
(2), (4) Date: Mar. 28, 2014

(87) PCT Pub. No.: WO2012/168928
PCT Pub. Date: Dec. 13, 2012

(65) Prior Publication Data
US 2014/0336489 A1    Nov. 13, 2014

(30) Foreign Application Priority Data

Jun. 10, 2011 (IT) .............................. TO2011A0516

(51) Int. Cl.
*A61B 18/04*     (2006.01)
*A61B 5/04*     (2006.01)
(Continued)

(52) U.S. Cl.
CPC ........ *A61B 5/04001* (2013.01); *A61B 5/6847* (2013.01); *A61B 5/6868* (2013.01);
(Continued)

(58) Field of Classification Search
CPC .. A61N 1/0551; A61N 1/0534; A61N 1/0456; A61N 1/0529; A61N 1/3606;
(Continued)

(56) References Cited

U.S. PATENT DOCUMENTS 3,841,310 A    10/1974  Goldstein
5,396,415 A *   3/1995  Konar .................. G05B 13/027
                                                    700/42
(Continued)

OTHER PUBLICATIONS

Fadiga, Luciano, 'ROBotic Open-architecture Technology for Cognition, Understanding and Behavior', RobotCub.Org , Aug. 31, 2009, pp. 1-26.
(Continued)

*Primary Examiner* — Joseph Stoklosa
*Assistant Examiner* — Brian M Antiskay
(74) *Attorney, Agent, or Firm* — The Belles Group, P.C.

(57) ABSTRACT

An intracortical-detection device including: at least one electrode that contacts a group of neurons; a first body, forming a surface that contacts a portion of a cerebral region; a first motor that moves the electrode with respect to the first body; a second motor; and a second body, operatively connected to the second motor, the first and second bodies being able to slide with respect to one another in a first direction, under the action of the second motor. The detection device moreover includes a sensor generating an electrical signal indicating a pressure exerted by the portion of cerebral region on the surface.

8 Claims, 7 Drawing Sheets (51) Int. Cl.
*A61N 1/00* (2006.01)
*A61B 90/11* (2016.01)
*A61B 90/00* (2016.01)
*A61B 5/00* (2006.01)
*A61B 17/00* (2006.01)
*A61B 90/10* (2016.01)

(52) U.S. Cl.
CPC ............ *A61B 5/6885* (2013.01); *A61B 90/06* (2016.02); *A61B 90/11* (2016.02); *A61B 5/4064* (2013.01); *A61B 2017/00022* (2013.01); *A61B 2090/065* (2016.02); *A61B 2090/103* (2016.02)

(58) Field of Classification Search
CPC ............. A61N 1/3605; A61N 1/36021; A61N 1/36025; A61N 1/36057; A61N 1/36067; A61N 1/36146; A61N 1/37205; A61N 1/0526; A61N 1/0531; A61N 1/0558; A61N 1/37247; A61N 1/04; A61B 5/04001; A61B 5/0476; A61B 5/6868; A61B 5/165; A61B 5/4094; A61B 5/742; A61B 5/0031; A61B 5/7282; A61B 5/0006; A61B 5/4064; A61B 18/14; A61B 2018/00184

USPC ........ 600/372–373, 377–378, 393, 544–545; 607/115–118; 606/22–32
See application file for complete search history.

(56) References Cited

U.S. PATENT DOCUMENTS

| | | | | |
|---|---|---|---|---|
| 5,569,166 | A * | 10/1996 | Stone | A61N 1/328 601/103 |
| 6,459,918 | B1 * | 10/2002 | Togashi | A61B 5/0478 600/378 |
| 7,277,742 | B2 * | 10/2007 | Putz | A61B 5/04001 600/378 |
| 2002/0010479 | A1 * | 1/2002 | Skakoon | A61B 34/20 606/130 |
| 2007/0156126 | A1 | 7/2007 | Flaherty | |

OTHER PUBLICATIONS

Corresponding PCT/IB2012/052948 Search Report and Written Opinion dated Oct. 19, 2012.

* cited by examiner

INTRACORTICAL-DETECTION DEVICE AND CORRESPONDING CONTROL METHOD

CROSS-REFERENCE TO RELATED PATENT APPLICATIONS

The present application is a U.S. national stage application under 35 U.S.C. §371 of PCT Application No. PCT/IB2012/052948, filed Jun. 11, 2012, which claims priority to Italian Application No. TO2011A000516, filed Jun. 10, 2011, the entireties of which are incorporated herein by reference.

TECHNICAL FIELD

The present invention relates to an intracortical-detection device and to the corresponding control method.

BACKGROUND ART

As is known, there are today available intracortical-detection systems, also known as recording or micro-recording systems. In particular, systems are known that resort to electrophysiological techniques based upon the use of miniaturized electrodes (micro-electrodes) in order to perform extracellular recordings in vivo. In practice, said systems make direct measurements of electrical quantities indicating the activity of groups of neurons, and consequently enable determination of information regarding the state of health of cerebral cortical portions.

Purely by way of example, in the case of patients affected by low-degree gliomas, current recording systems enable determination with high precision of the boundaries between normal cerebral tissue and pathological cerebral tissue. Consequently, the recording systems are finding increasingly wider use alongside diagnostic systems of a more traditional type.

By way of example, diagnostic systems of a traditional type comprise diagnostic systems that envisage determination of cerebral images on the basis of local measurements of the blood flow, such as for example positron-emission tomography (PET) and functional magnetic resonance imaging (fMRI), or else diagnostic systems that resort to electrophysiological techniques of measurement of the electrical activity of a very numerous neuronal population, such as for example electroencephalography (EEG), electrocorticography (ECoG) and magnetoencephalography (MEG). In general, said diagnostic systems do not present particularly fine spatial and temporal resolutions.

Figure 1:
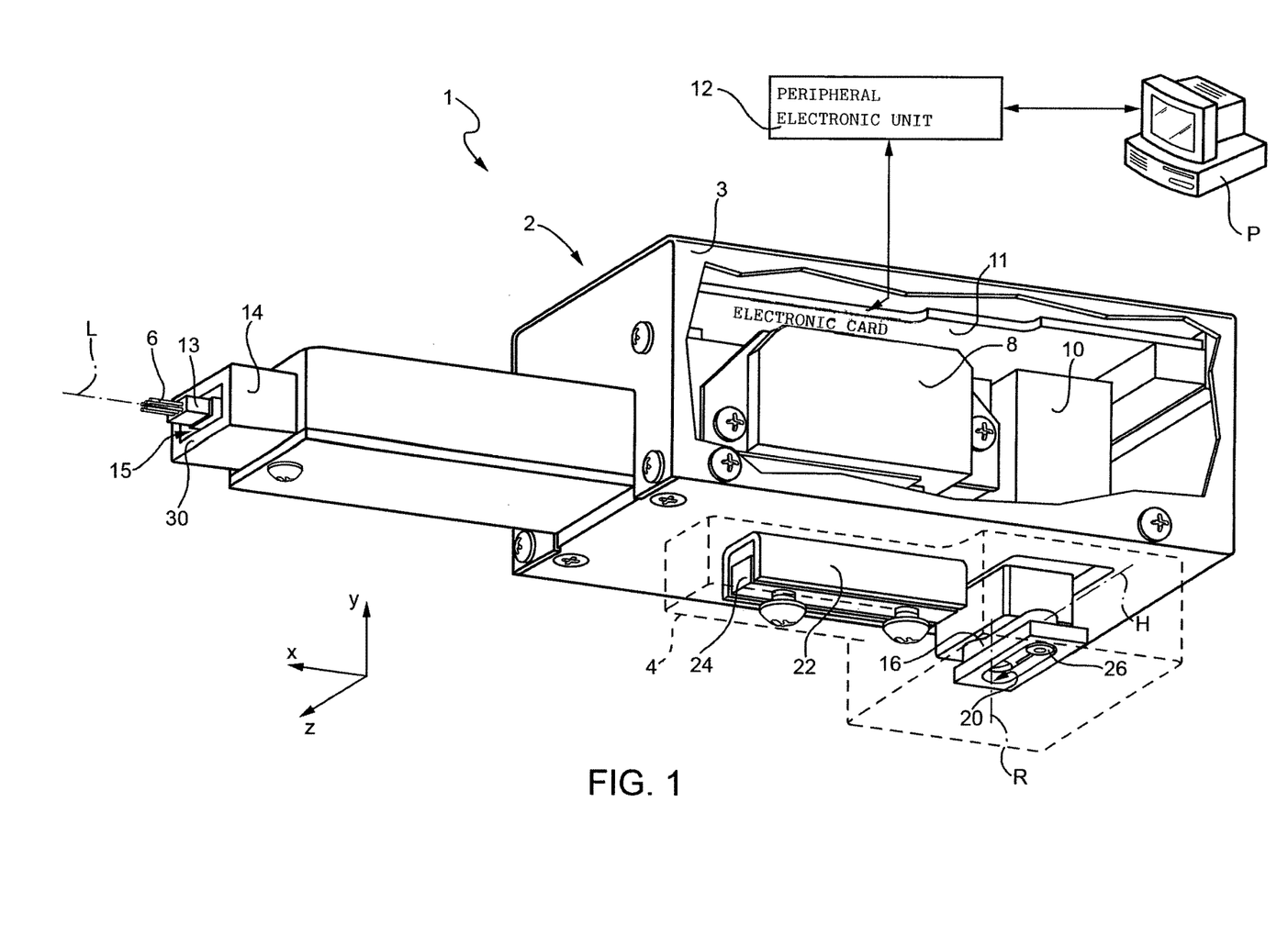
FIG. 1 shows a perspective view of an intracortical-detection system of a known type.

Amongst intracortical-detection systems, there is known the system illustrated in FIG. 1, referred to hereinafter as detection system 1.

In detail, the detection system 1 comprises an intracortical-detection device 2, known also as headstage and referred to hereinafter as detection device 2.

The detection device 2 comprises a first body 3 and a second body 4, arranged in contact with one another, as well as an array of electrodes 6, each of which is designed to contact a corresponding group of neurons in order to enable sensing of the corresponding electrical activity, as described hereinafter. For simplicity of illustration, in FIG. 1 the second body 4 is represented dashed.

The detection device 2 further comprises a first electric motor 8 and a second electric motor 10, as well as an electronic card 11, the latter being housed within the first body 3 and being electrically connected both to the first electric motor 8 and to the second electric motor 10 in order to govern operation thereof. The electronic card 11 is moreover electrically connected to the array of electrodes 6.

In turn, the electronic card 11 is electrically connectable to the outside world. In fact, the detection system 1 further comprises a control station P, which, in use, is connected to the electronic card 11, so that a user can govern, through the control station P, the electronic card 11 itself.

Typically, the connection between the electronic card 11 and the control station P is made by interposition of a peripheral electronic unit 12, which can include, among other things, a field programmable gate array (FPGA). The control of the first and second electric motors 8 and 10 by the user is hence mediated by the electronic card 11 and by the peripheral electronic unit 12.

The first electric motor 8 is a piezoelectric motor of the so-called "stick-and-slip" type, is housed within the first body 3, with respect to which it is fixed, and is coupled to the array of electrodes 6. Moreover, the first electric motor 8 is designed for moving the array of electrodes 6 parallel to a first direction x, in both senses, with a precision of 1 µm. In particular, the array of electrodes 6 is mobile along a longitudinal axis L of the detection device 2, parallel to the first direction x.

In detail, the array of electrodes 6 is constrained to a supporting structure 13, which is operatively coupled to the first electric motor 8 and is mobile under the action of the first electric motor 8, along the longitudinal axis L. Moreover, a portion of the first body 3 defines a contact element 14 having the shape, to a first approximation, of a hollow parallelepiped. The contact element 14 hence defines a cavity 15, inside which the supporting structure 13 and, consequently, the array of electrodes 6, can slide. The amount of this sliding can be set by the user through the control station P. Moreover, the position of the array of electrodes 6 is monitored electronically by means of an infrared marker and a three-dimensional optical tracking system (not illustrated).

As regards the second electric motor 10, it is in part housed within the first body 3, and in part within the second body 4. In particular, the second electric motor 10 is fixed with respect to the first body 3. Moreover, the second electric motor 10 is coupled to a crank 16 and is designed to move this crank 16 with circular motion.

More precisely, the crank 16 is made, for example, of aluminium, and has an elongated shape along a crank axis H, which joins a first end and a second end of the crank 16. In addition, the first end of the crank 16 is constrained to the second electric motor 10.

In practice, the second electric motor 10 is designed to cause the crank 16 to rotate about an axis of rotation R parallel to a second direction y, perpendicular to the crank axis H and to the first direction x.

Even more in particular, the electronic card 11 is able to govern the second electric motor 10 so that the crank 16 assumes any position within a pre-set range; this pre-set range is delimited by two extreme positions, which define an angle for example of ±30°, the angle 0° corresponding to the case where the crank axis H is perpendicular to the first direction x. The user hence cannot impose that the second electric motor 10 causes the crank 16 to rotate outside the pre-set range. This constraint is obtained, for example, by means of appropriate mechanical end-of-travel blocks (not illustrated).

The detection device 2 further comprises a groove 20, fixed with respect to the second body 4 and having an elongated shape, this groove 20 being parallel to a third direction z, perpendicular to the first direction x and the second direction y. Moreover, the detection device 2 comprises a guide 22, a slide 24, and a pin 26.

In detail, the pin 26 is fixed with respect to the crank 16. In particular, the pin 26 is constrained to the second end of the crank 16 and can hence rotate about the axis of rotation R under the action of the second electric motor 10. Moreover, the pin 26 co-operates with the groove 20; i.e., it is mechanically coupled thereto so as to exert a force on the walls of the groove 20 during its own movement about the axis of rotation R.

The guide 22 has an elongated shape and extends parallel to the first direction x. Moreover, the guide 22 is fixed with respect to the first body 3.

The slide 24 is housed within the guide 22. Moreover, the slide 24 can only translate linearly with respect to the guide 22, parallel to the first direction x. For this reason, between the guide 22 and the slide 24 there can be set a bearing (not illustrated).

The slide 24 is moreover fixed with respect to the second body 4, and hence is fixed also with respect to the groove 20. Consequently, following upon rotation, under the action of the second electric motor 10, of the crank 16, and hence of the pin 26, the first and second bodies 3, 4 translate linearly with respect to one another, parallel to the first direction x.

Operatively, the detection device 2 can find advantageous use in the course of a craniotomy, i.e., in the course of a surgical operation in which a portion of the brain of a patient is rendered surgically accessible to the outside world.

In these conditions, it is in fact possible to constrain the second body 4 to the skull of the patient by means of an appropriate mechanical arm (not illustrated) fixed with respect to the second body 4. In particular, the second body 4 is rendered fixed with respect to the skull of the patient, or to a support fixed with respect to the skull (for example, a structure fixed with respect to the operating table), in such a way that the contact element 14 contacts the brain of the patient, as well as in such a way that the first body 3 can move only in a direction parallel to the longitudinal axis L of the detection device 2.

Even more in particular, the contact element 14 defines a surface 30 having the shape of a hollow rectangle, which, in use, is traversed by the array of electrodes 6 and by the supporting structure 13. Moreover, the detection device 2 is constrained to the skull of the patient so that the surface 30 contacts a first portion of the cerebral region.

Next, it is possible to govern the first electric motor 8 so that the array of electrodes 6 translates until it comes into contact with a second portion of the cerebral region, surrounded by the first portion of cerebral region. Through the array of electrodes 6, the electronic card 11 can then acquire electrical signals emitted by the neurons, process them, and make them available to external electronic equipment. Possibly, processing of the electrical signals emitted by the neurons and acquired by the electrodes can be entrusted to the peripheral electronic unit 12.

In greater detail, during a craniotomy there occurs a continuous pulsation of the cerebral tissue due to the variation of the blood pressure caused by the heartbeat, which pumps the blood in an almost periodic way. Moreover, following upon the craniotomy, a sort of bulging of the brain is commonly found to occur.

Both pulsation of the cerebral tissue and bulging of the brain can lead to a deterioration of the quality of the electrical signals acquired by the electronic card 11. In particular, both pulsation of the cerebral tissue and bulging of the brain can modify the electrical signals acquired by the electronic card 11 through the array of electrodes 6, manifesting itself, from an electrical standpoint, in the form of electrical noise.

In order to preserve the quality of the electrical signals acquired by the electronic card 11, ensuring a contact with the outer surface of the brain and hence a spatial reference with respect to this surface, it is known to apply a static pressure in the first portion of cerebral region. In detail, this static pressure is exerted by means of the detection device 2 and in particular by means of the surface 30 of the contact element 14.

In greater detail, it is known to govern, by means of the control station P, the second electric motor 10 so that the first body 3 will translate with respect to the second body 4, the latter, as has been said, being constrained to the skull of the patient. In this way, the static pressure exerted by the surface 30 tends to counteract the bulging of the cerebral tissue.

In practice, typically it is the surgeon who governs, on the basis of his own experience, the motion of the surface 30, and then varies the pressure exerted thereby, without, however, having any information of a quantitative nature regarding the amount of pressure exerted by the cerebral tissue on the surface 30.

Consequently, typically the static pressure exerted by the surface 30 is lower or higher than an optimal pressure. In other words, typically the pressure exerted by the surface 30 is insufficient, or else is so high as to involve the risk that temporary ischaemias of the cerebral tissue might occur, i.e., dangerous interruptions of the bloodflow in the first portion of cerebral region.

DISCLOSURE OF INVENTION

The aim of the present invention is to provide an intracortical-detection device that will overcome at least in part the drawbacks of the known art.

According to the invention, an intracortical-detection device, an intracortical-detection system, and a control method are provided, as defined in Claims 1, 10 and 11, respectively.

BRIEF DESCRIPTION OF THE DRAWINGS

For a better understanding of the invention, embodiments thereof are now described, purely by way of non-limiting example, with reference to the attached drawings, wherein.

BEST MODE FOR CARRYING OUT THE INVENTION

Figure 2:
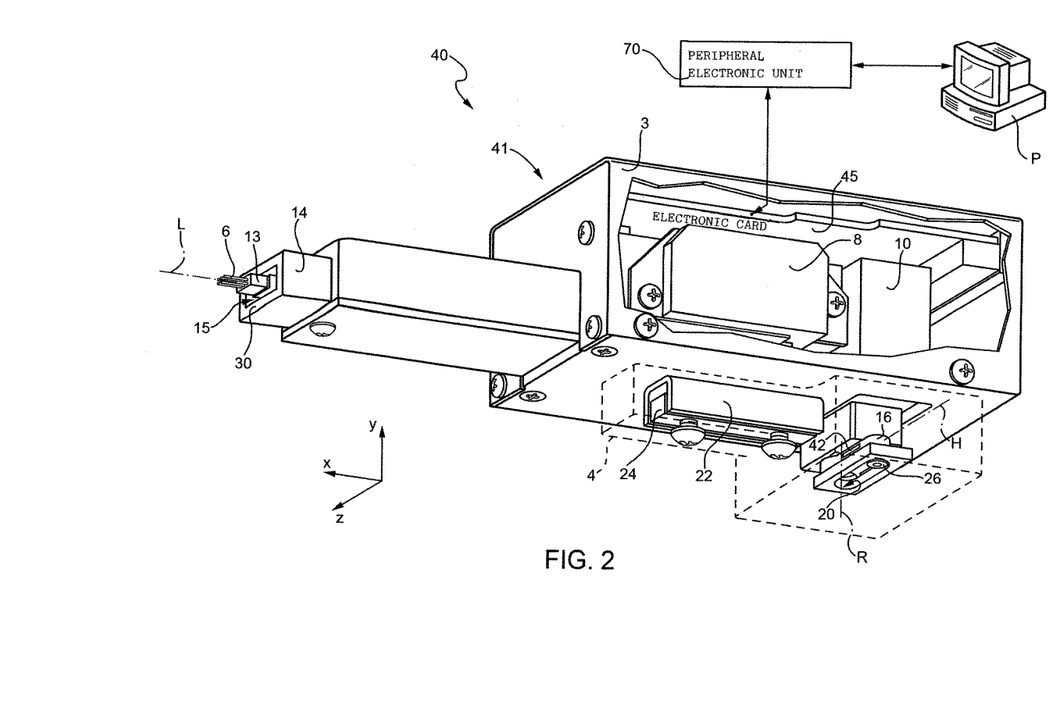
FIG. 2 shows a perspective view of an intracortical-detection system according to the present invention.

FIG. 2 shows an intracortical-detection system comprising an intracortical-detection device, referred to hereinafter as detection system 40 and detection device 41, respectively.

The detection system 40 and the detection device 41 are described hereinafter, the present description being limited just to the differences with respect to the detection system 1 and to the detection device 2 described previously and illustrated in FIG. 1. Moreover, components of the detection system 40 already present in the detection system 1 described previously are designated in the same way, except where otherwise specified.

In detail, the detection device 41 comprises a first strain gauge 42 and a second strain gauge 44 (illustrated in FIG. 3), of a type in itself known. In particular, each of the first and second strain gauges 42, 44 is a transducer that is able to vary its own electrical resistance as a function of a mechanical deformation to which it is subjected. Even more in particular, each of the first and second strain gauges 42, 44 can be formed, in a way in itself known, by a wire made of semiconductor material.

Figure 3:
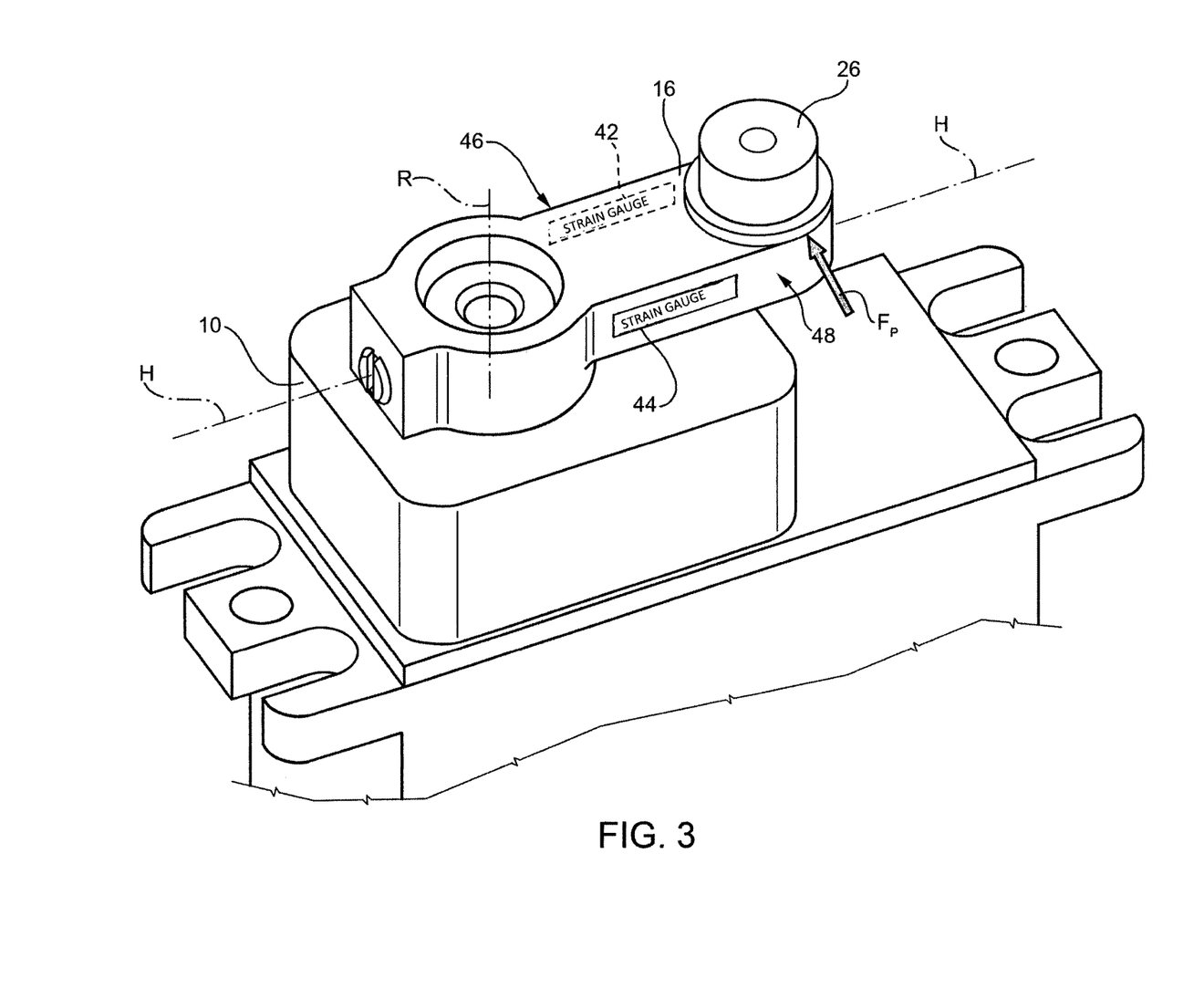
FIG. 3 shows a perspective view of a portion of the intracortical-detection system illustrated in FIG. 2.

As illustrated in greater detail in FIG. 3, the first and second strain gauges 42, 44 are arranged, respectively, on a first face 46 and a second face 48 of the crank 16 opposite to one another. In detail, the first and second faces 46, 48 are arranged parallel to the axis of rotation R and to the crank axis H, i.e., are parallel to the plane defined by this axis of rotation R and this crank axis H.

Figure 4:
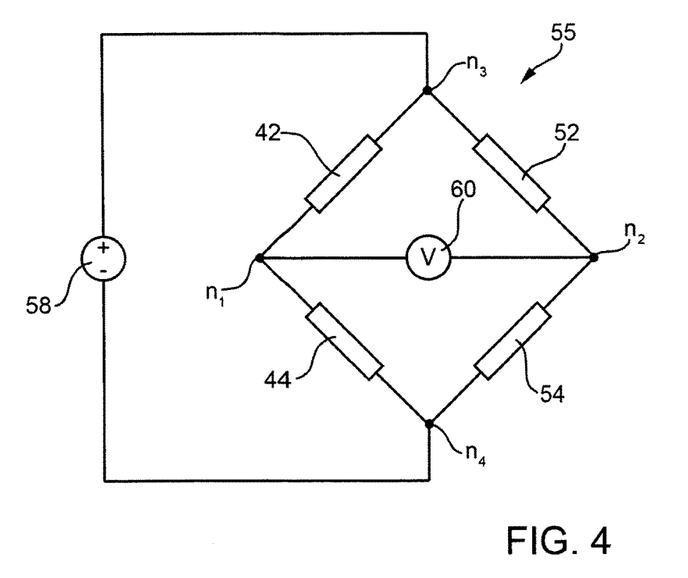
FIG. 4 shows an electrical diagram of a Wheatstone-bridge circuit.

Even though they are not illustrated, the first and second strain gauges 42, 44 are electrically connected to the electronic card, here designated by 45. Moreover, the electronic card 45 includes a first resistive element 52 and a second resistive element 54, which, as illustrated in FIG. 4, form, together with the first and second strain gauges 42, 44, a Wheatstone-bridge electrical circuit 55.

In detail, the first and second strain gauges 42, 44 are connected in a first reading node $n_1$, whilst the first and second resistive elements 52, 54 are connected in a second reading node $n_2$. Moreover, the first strain gauge 42 and the first resistive element 52 are connected in a first biasing node $n_3$, whilst the second strain gauge 44 and the second resistive element 54 are connected in a second biasing node $n_4$.

In greater detail, according to a possible embodiment, the first and second strain gauges 42, 44 are the same as one another and have a value of resistance at rest, i.e., in the absence of tensile or compressive forces, equal to $R_s$. Moreover, the first and second resistive elements 52, 54 both have a value of resistance equal to $R_s$.

The electronic card 45 moreover includes a voltage generator 58, which is connected between the first and second biasing nodes $n_3$, $n_4$ in such a way as to impose a biasing voltage between them. Moreover, the electronic card 45 comprises a voltage detector 60, which is connected between the first and second reading nodes $n_1$, $n_2$ and is designed to determine a reading voltage, present between the first and second reading nodes $n_1$, $n_2$. In other words, the voltage detector 60 is designed to supply an electrical read signal, indicating the voltage present between the first and second reading nodes $n_1$, $n_2$.

Operatively, the cerebral tissue exerts a pressure against the surface 30 of the contact element 14. Moreover, since the first and second bodies 3, 4 are mechanically coupled by means of the guide 22 and the slide 24, the first body 3 can move only in a direction parallel to the longitudinal axis L of the detection device 41; consequently, the pressure exerted by the cerebral tissue on the surface 30 is transmitted to the pin 26. As illustrated in FIG. 3, this means that the pin 26 is subject to a force $F_p$, which causes a deformation of the crank 16, and hence of the first and second faces 46, 48.

The deformation of the first and second faces 46, 48 causes a variation of the resistances of the first and second strain gauges 42, 44. In fact, we find that the resistance of one between the first and second strain gauges 42, 44 increases with respect to the value at rest, whereas the resistance of the other decreases. In particular, we find that one between the first and second strain gauges 42, 44 assumes a resistance equal to $R_s+R_p$, whereas the other assumes a resistance equal to $R_s-R_p$.

The reading voltage present between the first and second reading nodes $n_1$, $n_2$ is proportional to the resistance $R_p$, which depends linearly upon the force $F_p$. The electrical read signal supplied by the voltage detector 60 hence indicates the pressure exerted by the cerebral tissue on the surface 30 of the contact element 14.

Figure 5:
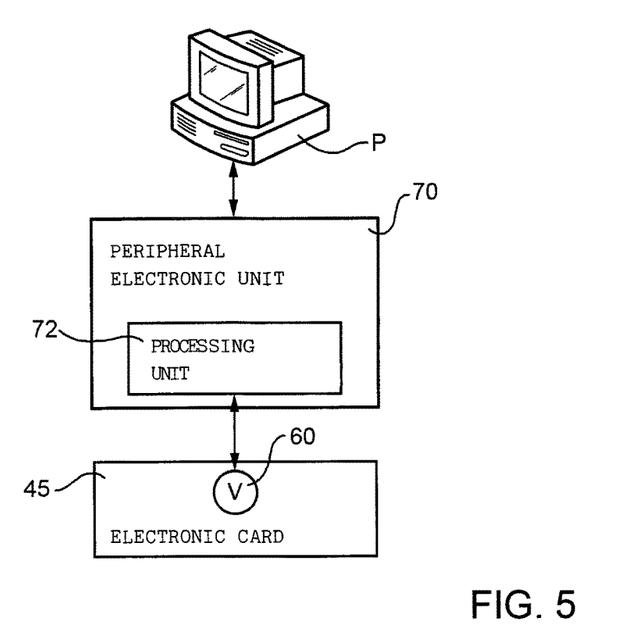
FIGS. 5, 6 and 7 show block diagrams regarding portions of the intracortical-detection system illustrated in FIG. 2.

As illustrated in FIG. 5, in a way in itself known, the electronic card 45 can supply the electrical read signal to the peripheral electronic unit, which is here and in FIG. 2 designated by 70.

In particular, the peripheral electronic unit 70 includes a processing circuit 72, electrically connected to the voltage detector 60 and designed to determine the pressure exerted by the cerebral tissue on the surface 30 of the contact element 14, on the basis of the electrical read signal supplied by the voltage detector 60. In detail, the processing circuit 72 generates an electrical measurement signal, which represents the pressure exerted by the cerebral tissue on the surface 30 of the contact element 14. In other words, the Wheatstone-bridge electrical circuit 55, the voltage detector 60, and the processing circuit 72 form an electrical pressure sensor.

The peripheral electronic unit 70 can thus supply to the control station P, to which it is connected, the electrical measurement signal, as determined by the processing circuit 72. In a way in itself known, the control station P includes a screen and is programmed to enable display on this screen of the values of the pressure exerted instant by instant by the cerebral tissue on the surface 30 of the contact element 14, as represented by the electrical measurement signal.

Thanks to the detection system 40, the surgeon can continuously have available quantitative information regarding the pressure exerted by the cerebral tissue on the surface 30, and can hence govern with greater precision the second electric motor 10, in order to apply on the first portion of cerebral region an initial static pressure adequate to guarantee contact between the surface 30 and the cerebral tissue, thus countering the bulging without inducing ischaemias.

Figure 6:
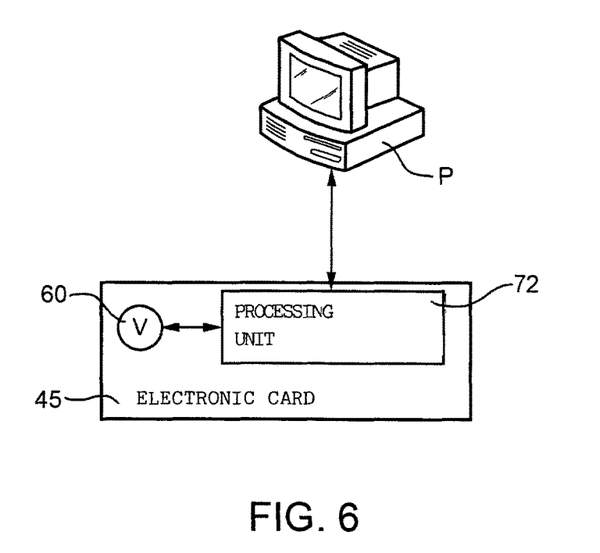

Alternatively, as illustrated in FIG. 6, the electronic unit can itself include the processing circuit 72, once again connected to the voltage detector 60. In this case, the processing circuit 72 can be directly connected to the control station P.

Figure 7:
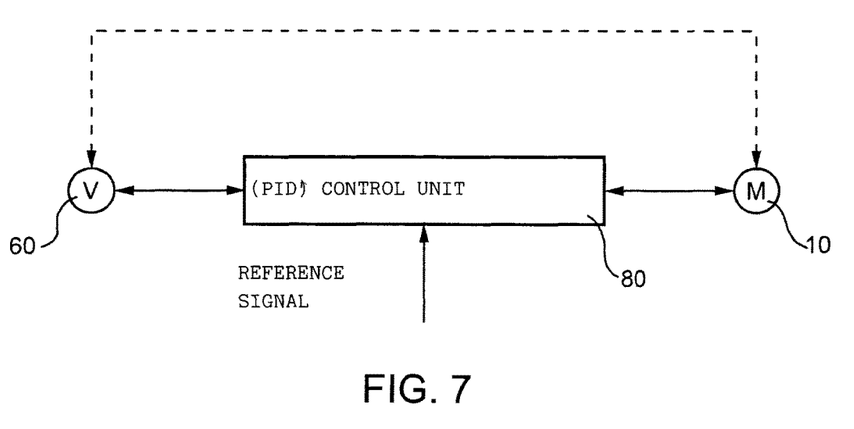

In order to enable also compensation of pulsations of the cerebral tissue, it is moreover possible to adopt the embodiment illustrated in FIG. 7. According to this embodiment, the electrical read signal supplied by the voltage detector 60 is used for controlling in closed loop the second electric motor 10, so that the position of the detection device 41, and in particular the position of the first body 3 with respect to the second body 4, adapts dynamically as a function of the instantaneous pressure exerted by the cerebral tissue on the surface 30.

In detail, according to this embodiment, the detection system 40 includes a control unit 80, which is of an electronic type and is electrically connected to the voltage detector 60 and to the second electric motor 10. In particular, the control unit 80 is arranged between the voltage detector 60 and the second electric motor 10. Moreover, the control unit 80 can be formed within the electronic card 45 or else within the peripheral electronic unit 70.

In greater detail, the control unit 80 governs the second electric motor 10 as a function of the electrical read signal generated by the voltage detector 60, i.e., as a function of the pressure exerted by the cerebral tissue on the surface 30.

In particular, in a way in itself known, the control unit 80 is designed to implement a control of the second electric motor 10 of the so-called "proportional-integral-derivative" (PID) type, on the basis of the electrical read signal supplied by the voltage detector 60 and of an electrical reference signal, which can be set by the user. For example, the electrical reference signal can be such that, in the (hypothetical) absence of pulsations, the pressure exerted by the surface 30 is equal to an optimal static pressure for the purposes of containment of bulging.

In other words, the voltage detector 60, the control unit 80, and the second electric motor 10 form a closed-loop control circuit of the second electric motor 10, since the electrical read signal supplied by the voltage detector 60 depends upon the position of the first body 3 with respect to the second body 4 and is hence affected by the operation of the second electric motor 10. Consequently, the second electric motor 10 is governed on the basis of a quantity (the reading voltage) that depends upon operation of the electric motor 10.

Operatively, the closed-loop control circuit causes the second electric motor 10 to be governed in such a way as to keep the pressure exerted by the surface 30 on the cerebral tissue constant. Equivalently, the second electric motor 10 is governed so that the relative position of the array of electrodes 6 with respect to the cerebral tissue does not vary on account of pulsation of the cerebral tissue. In other words, the array of electrodes 6 moves, under the action of the second electric motor 10, together with the first body 3, in such a way as to follow the movements of the cerebral tissue due to pulsation. In this way, not only is the position of the electrodes within the cerebral tissue kept constant, but moreover rubbing of the electrodes against the cerebral tissue in which they are inserted is limited, with consequent reduction of the electrical noise caused by this rubbing.

Figure 8:
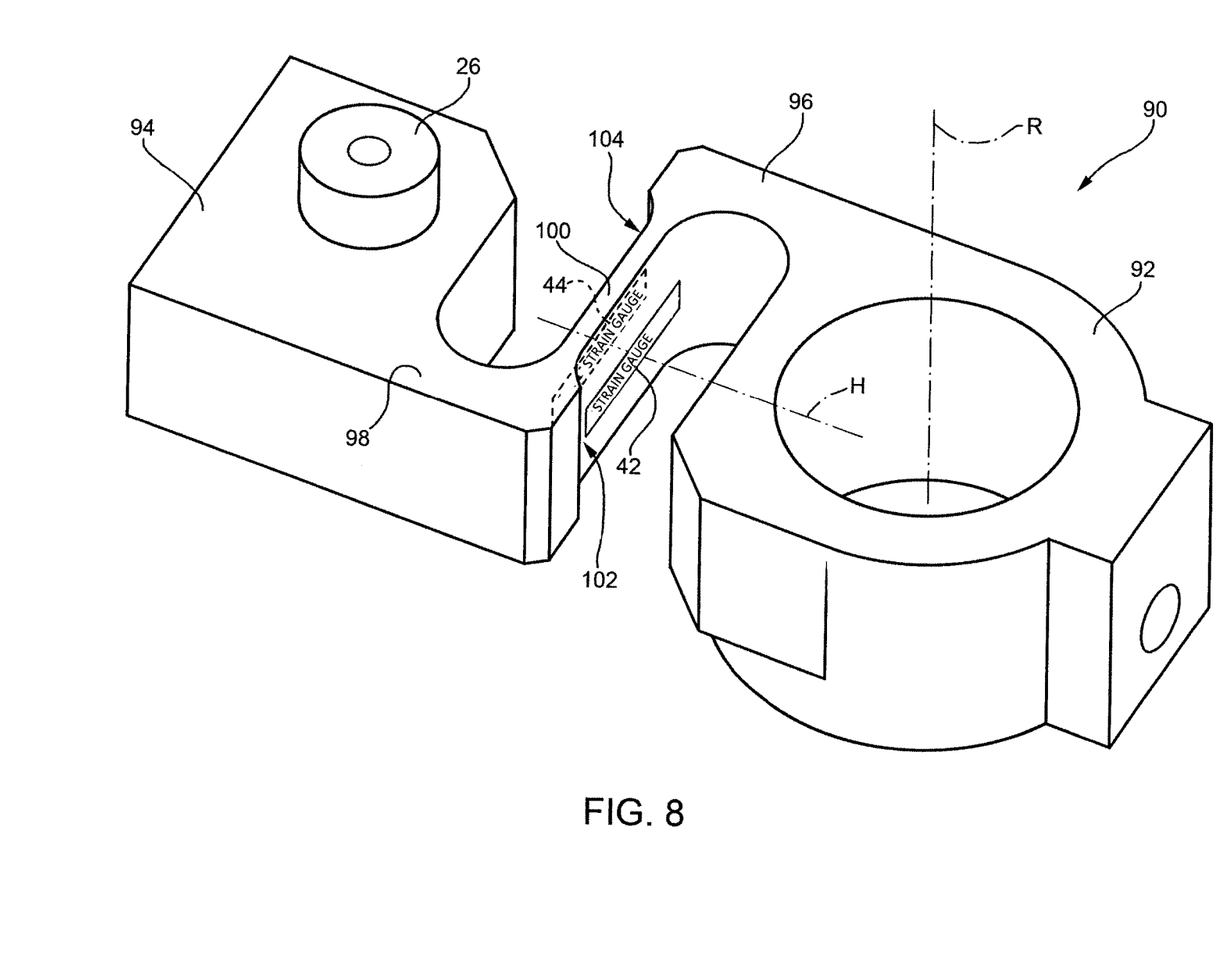
FIG. 8 is a perspective view of a variant of a crank of the intracortical-detection system illustrated in FIG. 2.

In order to increase the sensitivity of the first and second strain gauges 42, 44 with respect to the pressure exerted by the cerebral tissue on the surface 30, i.e., in order to increase the variation of resistance ($R_p$) of the first and second strain gauges 42, 44 given the same force $F_p$, it is moreover possible to adopt a crank of the type illustrated in FIG. 8, where it is designated by 90.

In detail, the crank 90 is elongated along the crank axis H and is S-shaped. Moreover, the crank 90 includes a first peripheral portion 92 and a second peripheral portion 94, which are arranged on the crank axis H and function respectively as first and second ends of the crank 90; the first and second peripheral portions 92, 94 are respectively constrained to the second electric motor 10 and to the pin 26, the latter being also here fixed with respect to the crank 90.

In greater detail, the first and second peripheral portions 92, 94 are connected by a first curved portion 96 and second curved portion 98, as well as by a plane portion 100, the latter being arranged between, and connected to, the first and second curved portions 96, 98. The first and second curved portions 96, 98 are moreover respectively connected, not only to the plane portion 100 but also to the first and second peripheral portions 92, 94.

The first and second peripheral portions 92, 94 have circular shapes, the centres of which are aligned along an axis parallel to the crank axis H. Moreover, the first and second curved portions 96 and 98 are arranged parallel to the crank axis H, and on opposite sides. The plane portion 100 defines a first face 102 and a second face 104, both plane and parallel to one another, and on which the first and second strain gauges 42, 44 are respectively arranged. In particular, the first and second faces 102, 104 are arranged perpendicular to the crank axis H, and parallel to the axis of rotation R about which the crank 90 turns.

Figure 9:
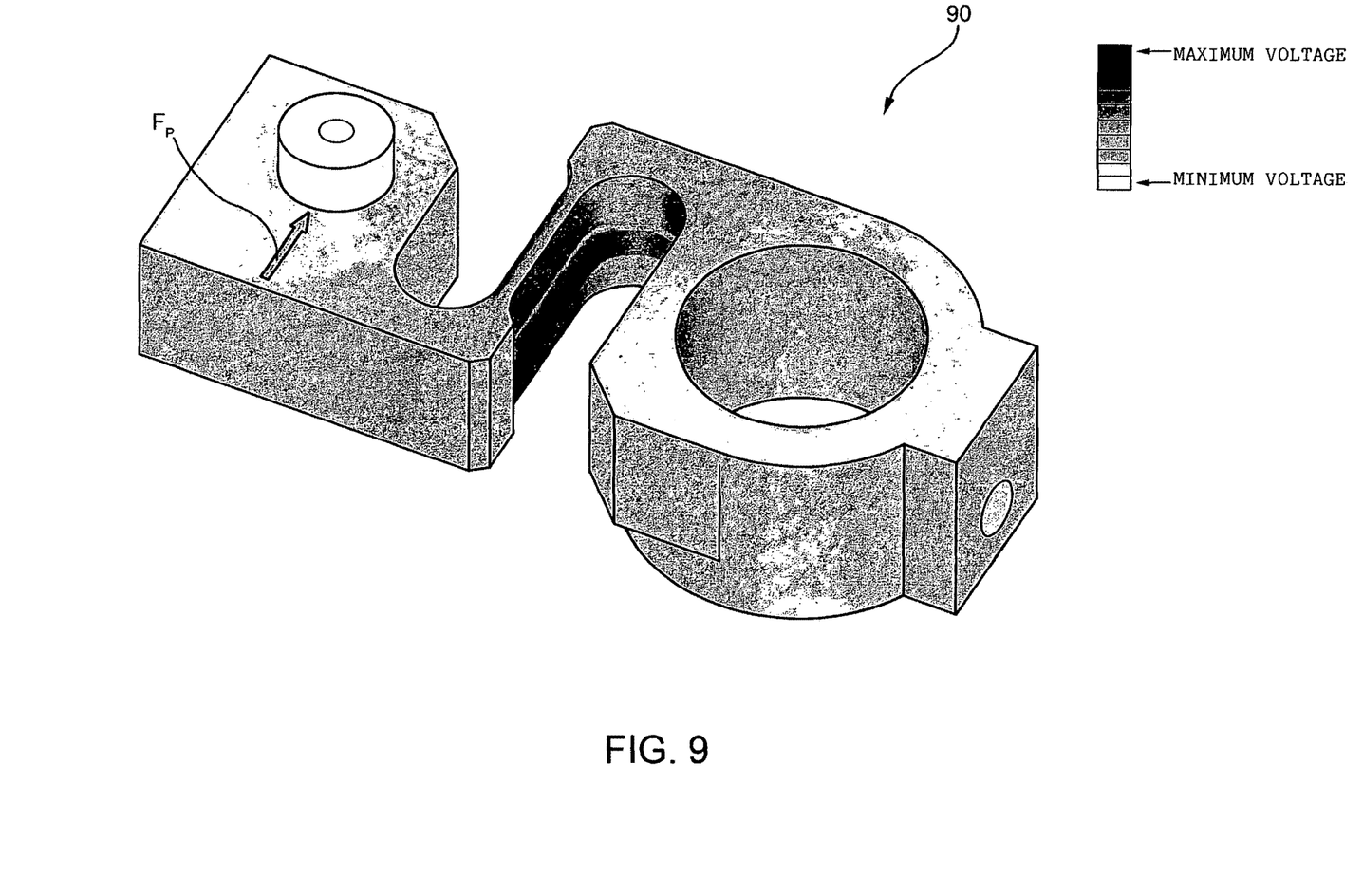
FIG. 9 shows qualitatively a distribution of the mechanical stresses along the crank illustrated in FIG. 8.

Given the same force $F_p$, the S-shaped crank 90 deforms more than the crank 16. Furthermore, the first and second faces 102, 104 are particularly subject to tensile/compressive stress following upon the action of the force $F_p$. As a demonstration of this, FIG. 9 shows qualitatively the distribution of the mechanical stresses along the crank 90. Consequently, given the same force $F_p$, the first and second strain gauges 42, 44 undergo a deformation greater than the case where they are constrained on the first face 46 and on the second face 48 of the crank 16. Consequently, the sensitivity of the electrical pressure sensor formed by the Wheatstone-bridge electrical circuit 55, by the voltage detector 60, and by the processing circuit 72 is increased.

The advantages that the present detection device affords emerge clearly from the foregoing description.

In particular, the present detection device makes it possible to provide the surgeon in real time with quantitative information on the pressure effectively exerted by the cerebral tissue on the surface 30 of the contact element 14, enabling him to regulate correctly the pressure exerted by the detection device 2 on the cerebral tissue.

In addition, according to the embodiment illustrated in FIG. 7, the instantaneous pressure exerted by the surface 30 on the cerebral tissue is kept substantially constant, irrespective of the pulsations of the cerebral tissue, which are precisely compensated dynamically in an automatic way thanks to the closed-loop control of the second electric motor 10. This compensation is made independently of the positioning of the array of electrodes 6 and moreover enables limitation of the electrical noise due to the relative motion of the array of electrodes 6 with respect to the cerebral tissue in which it is immersed.

Finally, it is evident that modifications and variations may be made to the present detection device, without thereby departing from the scope of the present invention.

For instance, instead of the first and second strain gauges 42, 44, transducers of a different type may be used, such as for example piezo-capacitive or piezo-resistive pressure sensors set on the surface 30. In addition, the arrangements of the first and second strain gauges 42, 44 may be different from what has been illustrated.

Likewise, variations may be made to the Wheatstone-bridge electrical circuit 55. For example, in a way in itself known, the electronic card 45 can control the voltage present on the second reading node $n_2$ in order to prevent saturation of the Wheatstone-bridge electrical circuit 55 due to the inevitable differences between the resistances of the first and second strain gauges 42, 44 and of the first and second resistive elements 52, 54. For this reason, the electronic card 45 can include a digital-to-analog converter (not illustrated) designed to impose, in a way in itself known, the voltage on the second reading node $n_2$.

It is likewise possible for the first and second strain gauges 42, 44 to form a circuit of a type different from the Wheatstone-bridge electrical circuit 55.

The invention claimed is:

1. An intracortical-detection device comprising: at least one electrode configured to contact a group of neurons; a first body, forming a surface configured to contact a portion of a cerebral region; a first motor configured to move said at least one electrode with respect to said first body; a second motor fixed with respect to said first body; and a second body, operatively connected to said second motor, said first and second bodies being able to slide with respect to one another in a first direction, under the action of said second motor; a sensor configured to generate an electrical signal indicating a pressure exerted by said portion of cerebral region on said surface; a crank, which is coupled to said second body and can be driven in rotation by said second motor about a second direction transverse with respect to said first direction; and a constraint configured to prevent motion of said first body with respect to said second body in directions different from said first direction; wherein said sensor comprises a transducer arranged on said crank and configured to vary an own electrical quantity as a function of a deformation of said crank caused by the pressure exerted by said portion of cerebral region on said surface.

2. The detection device according to claim 1, further comprising a control unit configured to govern said second motor as a function of said electrical signal.

3. The detection device according to claim 2, wherein said control unit is configured to control said second motor so that said surface exerts a substantially constant pressure on said portion of cerebral region.

4. The detection device according to claim 1, wherein said crank is S-shaped and defines a first face and a second face parallel to one another and parallel to said second direction, said transducer being arranged on said first and second faces.

5. The detection device according to claim 4, further comprising a groove fixed with respect to said second body and directed in a third direction transverse with respect to said first and second directions, and a pin, fixed with respect to said crank and co-operating with said groove; and wherein said crank includes a first end and a second end arranged in an axial direction and constrained to said second electric motor and to said pin, respectively, and an intermediate portion arranged between said first and second ends; and wherein said first and second faces are formed by said intermediate portion and are transverse with respect to said axial direction.

6. The detection device according to claim 4, wherein said transducer comprises a first strain gauge and a second strain gauge, arranged on said first and second faces, respectively.

7. The detection device according to claim 1, wherein said constraint comprises a guide, fixed with respect to said first body and parallel to said first direction, and a slide, fixed with respect to said second body and constrained to move along said guide.

8. An intracortical-detection system comprising an intracortical-detection device according to claim 1 and a display device, electrically connected to said sensor.

* * * * *

UNITED STATES PATENT AND TRADEMARK OFFICE
CERTIFICATE OF CORRECTION

PATENT NO.       : 9,848,792 B2
APPLICATION NO.  : 14/125058
DATED            : December 26, 2017
INVENTOR(S)      : Gian Nicola Angotzi, Luciano Fadiga and Giulio Sandini It is certified that error appears in the above-identified patent and that said Letters Patent is hereby corrected as shown below:

In the left column, Item (73), please correct the spelling of the Assignee name:
From:
FONDAZIONE INSTITUTO ITALIANO DI TECHNOLOGIA (IT)
To:
FONDAZIONE ISTITUTO ITALIANO DI TECNOLOGIA (IT)

Signed and Sealed this
Tenth Day of April, 2018

Andrei Iancu
*Director of the United States Patent and Trademark Office*